(12) United States Patent
Lips et al.

(10) Patent No.: US 10,316,169 B2
(45) Date of Patent: Jun. 11, 2019

(54) NOR-HALS COMPOUNDS AS FLAME RETARDANTS

(71) Applicant: BASF SE, Ludwigshafen (DE)

(72) Inventors: Gerard Lips, Huningue (FR); Gregor Huber, Basel (CH); Holger Hoppe, Loerrach (DE); Andre Le Gal, Huningue (FR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/700,748

(22) Filed: Sep. 11, 2017

(65) Prior Publication Data

US 2017/0369679 A1  Dec. 28, 2017

Related U.S. Application Data

(60) Division of application No. 15/131,585, filed on Apr. 18, 2016, now Pat. No. 9,783,655, which is a continuation of application No. 14/379,842, filed as application No. PCT/IB2013/052003 on Mar. 13, 2013, now abandoned.

(60) Provisional application No. 61/611,620, filed on Mar. 16, 2012.

(30) Foreign Application Priority Data

Mar. 16, 2012  (EP) .................... 12159919

(51) Int. Cl.
| | |
|---|---|
| *C08K 5/3435* | (2006.01) |
| *C07D 211/94* | (2006.01) |
| *C08K 5/00* | (2006.01) |
| *C08K 5/49* | (2006.01) |
| *C08K 5/5333* | (2006.01) |

(52) U.S. Cl.
CPC .......... *C08K 5/3435* (2013.01); *C07D 211/94* (2013.01); *C08K 5/0066* (2013.01); *C08K 5/49* (2013.01); *C08K 5/5333* (2013.01)

(58) Field of Classification Search
CPC .. C08K 5/3435; C08K 5/5333; C08K 5/0066; C07D 211/94
USPC ......................................................... 524/99
See application file for complete search history.

(56) References Cited

U.S. PATENT DOCUMENTS

| | | | |
|---|---|---|---|
| 3,030,331 A | 4/1962 | Goldberg | |
| 3,169,121 A | 2/1965 | Goldberg | |
| 4,130,458 A | 12/1978 | Moore et al. | |
| 4,263,201 A | 4/1981 | Mark et al. | |
| 4,286,083 A | 8/1981 | Kochanowski | |
| 4,552,704 A | 11/1985 | Mark | |
| 5,210,268 A | 5/1993 | Fukuoka et al. | |
| 5,606,007 A | 2/1997 | Sakashita et al. | |
| 6,660,787 B2 | 12/2003 | Mahood et al. | |
| 6,727,302 B2 | 4/2004 | Goossens et al. | |
| 6,730,720 B2 | 5/2004 | Gohr et al. | |
| 7,109,260 B2 | 9/2006 | Kaprinidis et al. | |
| 7,786,199 B2 | 8/2010 | Pauquet et al. | |
| 8,034,856 B2 | 10/2011 | Mizokawa et al. | |
| 8,329,787 B2 | 12/2012 | Negishi et al. | |
| 8,349,923 B2 | 1/2013 | Roth | |
| 2007/0228343 A1 | 10/2007 | Roth | |
| 2009/0111699 A1* | 4/2009 | Negishi ............... | C07D 211/94 504/361 |
| 2010/0249289 A1 | 9/2010 | Mizokawa et al. | |
| 2010/0249401 A1 | 9/2010 | Schoning | |
| 2011/0257310 A1* | 10/2011 | Butz ................... | C08K 5/5317 524/101 |
| 2012/0232197 A1 | 9/2012 | Menozzi et al. | |
| 2013/0023611 A1 | 1/2013 | Negishi et al. | |

FOREIGN PATENT DOCUMENTS

| | | |
|---|---|---|
| EP | 0 792 911 A2 | 9/1997 |
| EP | 1 731 508 A1 | 12/2006 |
| EP | 2 204 420 A1 | 7/2010 |
| EP | 2 210 918 A1 | 7/2010 |
| EP | 2 402 390 A1 | 1/2012 |
| JP | 2009-541428 A | 11/2009 |
| WO | WO 99/00450 A1 | 1/1999 |
| WO | WO 2004/035671 A1 | 4/2004 |
| WO | WO 2005/118697 A1 | 12/2005 |
| WO | WO 2008/003602 A1 | 1/2008 |
| WO | WO 2009/080554 A1 | 7/2009 |
| WO | WO 2011/003773 A1 | 1/2011 |
| WO | WO 2011/029744 A1 | 3/2011 |

OTHER PUBLICATIONS

International Search Report dated Aug. 15, 2013 in PCT/IB2013/052003.
European Search Report dated Sep. 28, 2012 in Patent Application No. 12 15 9919.
Office Action dated Nov. 5, 2018 in Japanese Patent Application No. 2017-148869 (with English language translation).

* cited by examiner

*Primary Examiner* — Hui H Chin
(74) *Attorney, Agent, or Firm* — Oblon, McClelland, Maier & Neustadt, L.L.P.

(57) ABSTRACT

The present invention relates to the use of NOR-HALS compounds in flame retardant polymer compositions. These compositions are especially useful for the manufacture of flame retardant compositions based on thermoplastic polymers, especially polyolefin homo- and copolymers, polycondensates, such as polyamines or polyesters and duroplastic polymers, such as polyepoxides.

8 Claims, No Drawings

NOR-HALS COMPOUNDS AS FLAME RETARDANTS

CROSS-REFERENCE TO RELATED APPLICATIONS

The application is a divisional application of U.S. Ser. No. 15/131,585, filed Apr. 18, 2016, which is a continuation of U.S. Ser. No. 14/379,842, filed Aug. 20, 2014, which is a 371 of PCT/IB2013/052003, filed Mar. 13, 2013, which claims priority to EP 12159919.5, filed Mar. 16, 2012, and claims benefit of provisional to 61/611,620, filed Mar. 16, 2012.

The present invention relates to the use of NOR-HALS compounds in flame retardant polymer compositions. These compositions are especially useful for the manufacture of flame retardant compositions based on thermoplastic polymers, especially polyolefin homo- and copolymers, polycondensates, such as polyamines or polyesters, and duroplastic polymers, such as polyepoxides.

Flame retardants are added to polymeric materials (synthetic or natural) to enhance the flame retardant properties of the polymers. Depending on their composition, flame retardants may act in the solid, liquid or gas phase either chemically, e.g. as a spumescent by liberation of nitrogen, and/or physically, e.g. by producing a foam coverage. Flame retardants interfere during a particular stage of the combustion process, e.g. during heating, decomposition, ignition or flame spread.

There is still a need for flame retardant compositions with improved properties that can be used in different polymer substrates. Increased standards with regard to safety and environmental requirements result in stricter regulations. Particularly known halogen containing flame retardants no longer match all necessary requirements. Therefore, halogen free flame retardants are preferred, particularly in view of their better performance in terms of smoke density associated with fire. Improved thermal stability and less corrosive behaviour are further benefits of halogen free flame retardant compositions.

NOR-HALS compounds are known from EP 1 731 508 as stabilizers for synthetic resins to protect these substrates from degradation caused by the action of chemicals and acid rain.

It has surprisingly been found that thermoplastic or duroplastic polymers with excellent flame retardant properties are prepared in the event that selected NOR-HALS compounds are added to the polymer substrate.

These compositions have excellent thermal stability and are therefore especially suited for the application in engineering thermoplastics and epoxy laminates used for the manufacture of electrical and electronic parts and devices. By using the instant flame retardant additives in thermoplastic and duroplastic resins, conventional halogen containing flame retardants and halogenated epoxy resins, antimony compounds, and inorganic fillers may largely be reduced or replaced.

The present invention relates to the use of a NOR-HALS compound of the formula

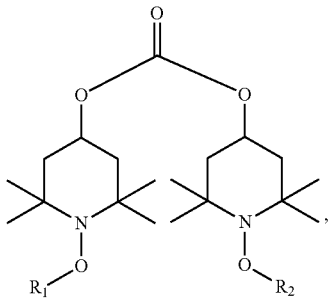

Wherein
$R_1$ and $R_2$ represent $C_1$-$C_{30}$alkyl,
for inducing the flame retardancy in polymers.

Examples of $C_1$-$C_{30}$alkyl groups represented by $R_1$ and $R_2$ in the above formula (I) are linear, or where possible, branched alkyl groups, such as methyl, ethyl, n-propyl, isopropyl, n-butyl, tert-butyl, isobutyl, n-pentyl, sec-pentyl, tert-pentyl, n-hexyl, isohexyl, n-heptyl, n-octyl, iso-octyl, 2-ethylhexyl, tert-octyl, n-nonyl, isononyl, n-decyl, n-undecyl, n-dodecyl (lauryl), n-tridecyl, n-tetradecyl (myristyl), n-pentadecyl, n-hexadecyl (cetyl), n-octadecyl etc.

The polymer compositions wherein the compounds (I), as defined above, are present, attain the desirable ratings related established flame retardant test methods, especially in polyolefin compositions.

This compound (I) is preferably contained in the flame retardant compositions according to the invention in an amount from about 0.005-90.0 wt. %, preferably about 0.02-20.0 wt. %, most preferably between 0.10-15.0 wt.-%, based on the total weight of the composition.

The term polymer and substrate comprises within its scope thermoplastic and duro-plastic polymers and thermosets.

A list of suitable thermoplastic polymers is given below:
1. Polymers of monoolefins and diolefins, for example thermoplastic polyolefins (TPO), such as polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be cross linked), for example high density polymethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE). Polyolefins, i.e. the polymers of monoolefins exemplified in the preceding paragraph, preferably polyethylene and polypropylene, can be prepared by different and especially by the following methods:
    a) Radical polymerisation (normally under high pressure and at elevated temperature).
    b) Catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either α- or π-bond coordinated. These metal complexes may be in the free form or fixed on substrates, typically on activated magnesium chloride, titanium (III) chloride, and alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, and amine or silyl ether groups. These catalyst systems are usually termed Phillips, Standard Oil Indiana, Ziegler-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclo-hexene copolymers, ethylene/alkyl acrylate copolymers, such as ethylene-n-butyl acrylate or methacrylate, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch;

The homopolymers and copolymers mentioned above may have a stereo structure including syndiotactic, isotactic, hemi-isotactic or atactic; where atactic polymers are preferred. Stereo block polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyl toluene, all isomers of ethyl styrene, propyl styrene, vinyl biphenyl, vinyl naphthalene, and vinyl anthracene, and mixtures thereof. Homopolymers and copolymers may have a stereo structure including syndiotactic, isotactic, hemi-isotactic or atactic; where atactic polymers are preferred. Stereo block polymers are also included;
  a) Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/iso-prene/styrene, styrene/ethylene/butylene/styrene or styrene/ethylene/propy-lene/styrene.
  b) Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).
  c) Hydrogenated aromatic polymers derived from hydrogenation of polymers mentioned under 6a). Homopolymers and copolymers may have a stereo structure including syndiotactic, isotactic, hemi-isotactic or atactic; where atactic polymers are preferred. Stereo block polymers are also included.

7. Graft copolymers of vinyl aromatic monomers, such as styrene or α-methylstyrene, for example styrene on polybutadiene, styrene on polybutadiene-styrene or poly-butadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulphochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/ alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1 above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes, which contain ethylene oxide as a co-monomer; polyacetals modified with thermoplastic polyurethanes, acrylates or MBS.
14. Polyphenylene oxides and sulphides, and mixtures of polyphenylene oxides with styrene polymers or polyamides.
15. Polyamides and co-polyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or co-polyamides modified with EPDM or ABS; and poly-amides condensed during processing (RIM polyamide systems).
16. Polyureas, polyimides, polyamide imides, polyether imides, polyester imides, polyhydantoins and polybenzimidazoles.
17. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block co-polyether esters derived from hydroxyl-terminated polyethers; and also polyesters modified with polycarbonates or MBS.
18. Polyketones.
19. Polysulphones, polyether sulphones and polyether ketones.
20. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
21. Polycarbonates that correspond to the general formula:

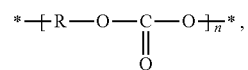

Such polycarbonates are obtainable by interfacial processes or by melt processes (catalytic transesterification). The polycarbonate may be either branched or linear in structure and may include any functional substituents. Polycarbonate copolymers and polycarbonate blends are also within the scope of the invention. The term polycarbonate should be interpreted as inclusive of copolymers and blends with other thermoplastics. Methods for the manufacture of polycarbonates are known, for example, from U.S. Pat. Nos. 3,030,331; 3,169,121; 4,130,458; 4,263,201; 4,286,083; 4,552,704; 5,210,268; and 5,606,007. A combination of two or more polycarbonates of different molecular weights may be used.

Preferred are polycarbonates obtainable by reaction of a diphenol, such as bisphenol A, with a carbonate source. Examples of suitable diphenols are:

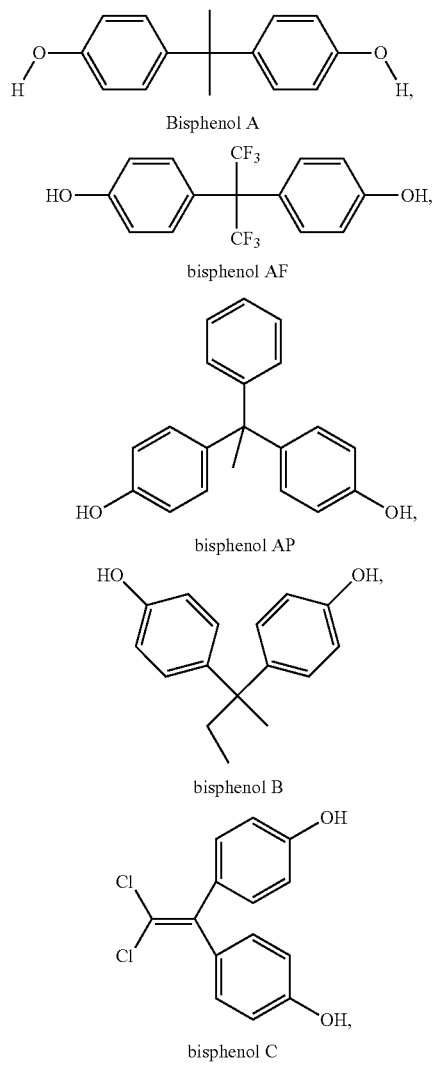

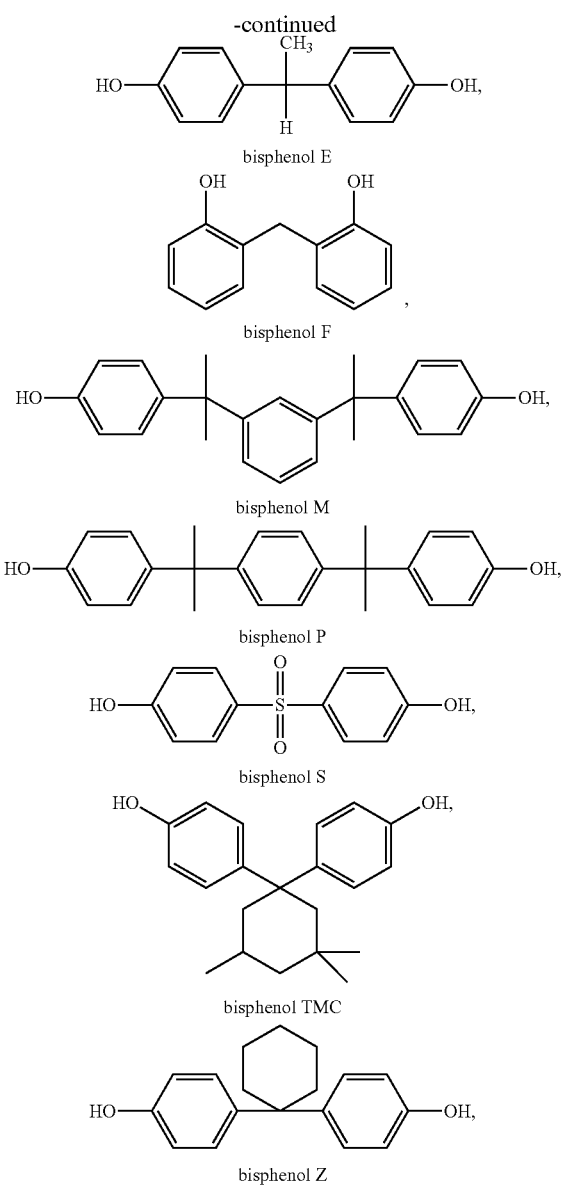

4,4'-(2-norbornylidene)bis(2,6-dichlorophenol); or fluorene-9-bisphenol:

The carbonate source may be a carbonyl halide, a carbonate ester or a haloformate. Suitable carbonate halides are phosgene or carbonylbromide. Suitable carbonate esters are dialkylcarbonates, such as dimethyl- or diethylcarbonate, diphenyl carbonate, phenyl-alkylphenylcarbonate, such as phenyl-tolylcarbonate, dialkylcarbonates, such as dimethyl- or diethylcarbonate, di-(halophenyl)carbonates, such as di-(chlorophenyl)carbonate, di-(bromophenyl)carbonate, di-(trichlorophenyl)carbonate or di-(trichlorophenyl)carbonate, di-(alkylphenyl)carbonates, such as di-tolylcarbonate, naphthylcarbonate, dichloronaphthylcarbonate and others.

The polymer substrate mentioned above, which comprises polycarbonates or polycarbonate blends is a polycarbonate-copolymer, wherein isophthalate/terephthalate-resorcinol segments are present. Such polycarbonates are commercially available, e.g. Lexan® SLX (General Electrics Co. USA). Other polymeric substrates of component b) may additionally contain in the form as admixtures or as copolymers a wide variety of synthetic polymers including polyolefins, polystyrenes, polyesters, polyethers, polyamides, poly(meth)acrylates, thermoplastic polyurethanes, polysulphones, polyacetals and PVC, including suitable compatibilizing agents. For example, the polymer substrate may additionally contain thermoplastic polymers selected from the group of resins consisting of polyolefins, thermoplastic polyurethanes, styrene polymers and copolymers thereof. Specific embodiments include polypropylene (PP), polyethylene (PE), polyamide (PA), polybutylene terephthalate (PBT), polyethylene terephthalate (PET), glycol-modified polycyclohexylenemethylene terephthalate (PCTG), polysulphone (PSU), polymethylmethacrylate (PMMA), thermoplastic polyurethane (TPU), acrylonitrile-butadiene-styrene (ABS), acrylonitrile-styrene-acrylic ester (ASA), acrylonitrile-ethylene-propylene-styrene (AES), styrene-maleic anhydride (SMA) or high impact polystyrene (HIPS).

A preferred embodiment of the invention relates to the use of NOR-HALS compounds (I) in thermoplastic polymers. Preferred thermoplastic polymers include polyamides, polyesters and polycarbonates.

Another preferred embodiment of the invention relates to a composition, wherein component c) is a duroplastic polymer substrate of the polyepoxide type.

A particularly preferred embodiment of the invention relates to the use of a NOR-HALS compound (I), wherein $R_1$ and $R_2$, independently of one another, represent n-butyl, n-undecyl or n-octadecyl, for inducing flame retardancy in polymers.

A highly preferred embodiment of the invention relates to the use of a NOR-HALS compound (I), wherein $R_1$ and $R_2$ represent n-undecyl, for inducing flame retardancy in polymers.

A further embodiment of the invention relates to a composition, which comprises a) At least one NOR-HALS compound of the formula (I)

Wherein

R$_1$ and R$_2$ represent C$_1$-C$_{30}$alkyl;

b) At least one flame retardant compound selected from the group consisting of tris(tribromoneopentyl)phosphate:

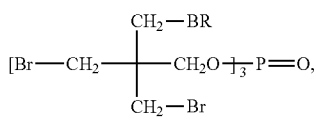

resorcinol-bis-diphenylphosphate:

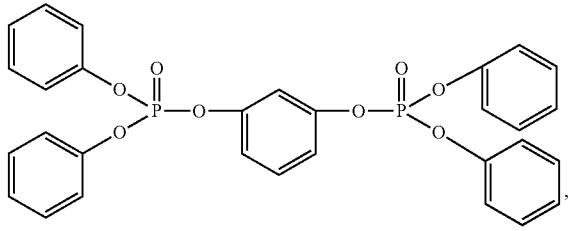 [SMILES: O=P(Oc1ccccc1)(Oc1ccccc1)Oc1cccc(OP(=O)(Oc2ccccc2)Oc2ccccc2)c1]

pentaerythritol-di-methyl phosphonate:

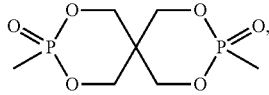

guanidine phenylphosphonate, melamine phenylphosphonate, dimethylaluminium phosphinate, methyl-ethylaluminiumphosphinate, diethylaluminiumphosphinate, poly-[2,4-(piperazine-1,4-yl)-6-morpholine-4-yl)-1,3,5-triazine] and ammonium polyphosphate; and c) A polymer substrate.

The use of the composition defined above for inducing the flame retardancy in polymers is also subject matter of the present invention.

Another preferred embodiment relates to a composition, which comprises a) At least one NOR-HALS compound (I), wherein R$_1$ and R$_2$ represent n-undecyl;

b) At least one flame retardant compound selected from the group consisting of tris(tribromoneopentyl)phosphate, resorcinol-bis-di phenylphosphate, pentaerythritol-di-methyl phosphonate, guanidine phenylphosphonate, melamine phenylphosphonate, dimethylaluminium phosphinate, methyl-ethylaluminiumphosphinate, diethylaluminiumphosphinate, poly-[2,4-(piperazine-1,4-yl)-6-morpholine-4-yl)-1,3,5-triazine] and aluminum polyphosphate; and c) A polymer substrate.

The combination of the NOR-HALS (I) and the additional flame retardants defined above is preferably contained in the flame retardant compositions according to the use defined above in an amount from about 0.005-90.0 wt. %, preferably about 0.02-20.0 wt. %, most preferably between 0.10-15.0 wt.-%, based on the total weight of the composition.

The instant invention further pertains to the use of compounds (I) in flame retardant compositions and to the above-defined compositions which comprise, in addition to the components defined above, optional components, such as additional flame retardants and/or further additives selected from the group consisting of tetraalkylpiperidine additives, smoke suppressants, polymer stabilizers, fillers, reinforcing agents and so-called anti-dripping agents that reduce the melt flow of thermoplastic polymers and reduce the formation of drops at higher temperatures.

Such additional flame retardants are phosphorus containing flame retardants, for example selected from the group consisting of phosphorus and/or nitrogen containing flame retardants, organo-halogen containing flame retardants and inorganic flame retardants.

Phosphorus containing flame retardants are, for example, resorcinol phenylphosphate oligomer (Fyrolflex® RDP, Akzo Nobel), triphenyl phosphate, bisphenol A phenylphosphate oligomer (Fyrolflex® BDP), tris(2,4-di-tert-butylphenyl)phosphate, ethylenediamine diphosphate (EDAP), tetra (2,6-dimethylphenyl) resorcinol diphosphate, diethyl-N,N-bis(2-hydroxyethyl)-aminomethyl phosphonate, hydroxyalkyl esters of phosphorus acids, salts of hypophosphoric acid (H$_3$PO$_2$), particularly the Ca$^{2+}$, Zn$^{2+}$, or Al$^{3+}$ salts, tetrakis(hydroxymethyl)phosphonium sulphide, triphenylphosphine, triphenyl phosphine oxide, tetraphenyldiphosphine monoxide, phosphazenes and 9,10-dihydro-9-oxa-10-phosphorylphenanthrene-10-oxide (DOPO) and its derivatives, such as 2-(9,10-dihydro-9-oxa-10-phosphaphenanthrene-10-oxide)-1,4-benzenediol.

Nitrogen containing flame retardants are, for example, isocyanurate flame retardants, such as polyisocyanurate, esters of isocyanuric acid or isocyanurates. Representative examples are hydroxyalkyl isocyanurates, such as tris-(2-hydroxyethyl)isocyanurate, tris(hydroxymethyl)isocyanurate, tris(3-hydroxy-n-proyl)isocyanurate or triglycidyl isocyanurate.

Nitrogen containing flame-retardants furthermore include melamine-based flame retardants. Representative examples are: melamine cyanurate, melamine borate, melamine phosphate, melamine pyrophosphate, melamine polyphosphate, melamine ammonium polyphosphate, melamine ammonium pyrophosphate, dimelamine phosphate and dimelamine pyrophosphate.

Further examples are: benzoguanamine, allantoin, glycoluril, urea cyanurate, ammonium polyphosphate, and a condensation product of melamine from the series melem, melam, melon and/or a higher condensed compound or a reaction product of melamine with phosphoric acid or a mixture thereof.

Representative organo-halogen flame retardants are, for example:

Polybrominated diphenyl oxide (DE-60F, Chemtura Corp.), decabromodiphenyl oxide (DBDPO; Saytex® 102E), tris[3-bromo-2,2-bis(bromomethyl)propyl] phosphate (PB 370®, FMC Corp.), tris(2,3-dibromopropyl)phosphate, tris(2,3-dichloropropyl)phosphate, chlorendic acid, tetrachlorophthalic acid, tetrabromophthalic acid, polychloroethyl triphosphonate mixture, tetrabromobisphenol A bis (2,3-dibromopropyl ether) (PE68), brominated epoxy resin, ethylene-bis(tetrabromophthalimide) (Saytex® BT-93), bis (hexachlorocyclopentadieno)cyclooctane (Declorane Plus®), chlorinated paraffins, octa-bromodiphenyl ether, 1,2-bis(tribromophenoxy)ethane (FF680), tetrabromo-bisphenol A (Saytex® RB100), ethylene bis-(dibromo-norbornanedicarboximide) (Saytex® BN-451), bis-(hexachlorocyclopentadieno) cyclooctane, PTFE, tris-(2,3-dibromopropyl)-isocyanurate, and ethylene-bis-tetrabromophthalimide.

The organohalogen flame retardants mentioned above are routinely combined with an inorganic oxide synergist. Most common for this use are zinc or antimony oxides, e.g. $Sb_2O_3$ or $Sb_2O_5$. Boron compounds are suitable, too.

Representative inorganic flame retardants include, for example, aluminium trihydroxide (ATH), boehmite (AlOOH), magnesium dihydroxide (MSH), hydrotalcite, zinc borates, $CaCO_3$, (organically modified) layered silicates, (organically modified) layered double hydroxides, and mixtures thereof.

The above-mentioned additional flame retardant classes are advantageously contained in the composition of the invention in an amount from about 0.5% to about 75.0% by weight of the organic polymer substrate; for instance about 10.0% to about 70.0%; for example about 25.0% to about 65.0% by weight, based on the total weight of the composition.

According to another embodiment, the invention relates to compositions which additionally comprise as additional component so-called anti-dripping agents.

These anti-dripping agents reduce the melt flow of the thermoplastic polymer and inhibit the formation of drops at high temperatures. Various references, such as U.S. Pat. No. 4,263,201, describe the addition of anti-dripping agents to flame retardant compositions.

Suitable additives that inhibit the formation of drops at high temperatures include glass fibres, polytetrafluoroethylene (PTFE), high temperature elastomers, carbon fibres, glass spheres and the like.

The addition of polysiloxanes of different structures has been proposed in various references; cf. U.S. Pat. Nos. 6,660,787, 6,727,302 or 6,730,720.

According to a further embodiment, the invention relates to compositions which additionally comprise as additional components fillers and reinforcing agents. Suitable fillers are, for example, glass powder, glass microspheres, silica, mica, wollastonite and talcum.

Stabilizers are preferably halogen-free and selected from the group consisting of nitroxyl stabilizers, nitrone stabilizers, amine oxide stabilizers, benzofuranone stabilizers, phosphite and phosphonite stabilizers, quinone methide stabilizers and monoacrylate esters of 2,2'-alkylidenebisphenol stabilizers.

As mentioned above, the composition according to the invention may additionally contain one or more conventional additives, for example selected from the group consisting of pigments, dyes, plasticizers, antioxidants, thixotropic agents, levelling assistants, basic co-stabilizers, metal passivators, metal oxides, organophosphorus compound, UV-absorbers and further light stabilizers and mixtures thereof, especially pigments, phenolic antioxidants, calcium stearate, zinc stearate and UV absorbers of the 2-hydroxybenzophenone, 2-(2'-hydroxyphenyl)benzotriazole and/or 2-(2-hydroxyphenyl)-1,3,5-triazine and benzoate groups, such as 2,4-Di-tert-butylphenyl 3,5-di-tert-butyl-4-hydroxybenzoate (TINUVIN 120) or hexadecyl 3,5-bis-tert-butyl-4-hydroxybenzoate (Cytec Cyasorb®UV 2908.

Preferred additional additives for the compositions as defined above are processing stabilizers, such as the above-mentioned phosphites and phenolic antioxidants, and light stabilizers, such as benzotriazoles. Preferred specific antioxidants include octadecyl 3-(3,5-di-tert-butyl-4-hydroxyphenyl) propionate (IRGANOX 1076), pentaerythritol-tetrakis[3-(3,5-di-tert-butyl-4-hydroxyphenyl)propionate] (IRGANOX 1010), tris(3,5-ditert-butyl-4-hydroxyphenyl) isocyanurate (IRGANOX 3114), 1,3,5-trimethyl-2,4,6-tris (3,5-di-tert-butyl-4-hydroxybenzyl)benzene (IRGANOX 1330), triethyleneglycol-bis[3-(3-tert-butyl-4-hydroxy-5-methylphenyl)propionate] (IRGANOX 245), and N,N'-hexane-1,6-diyl-bis[3-(3,5-di-tert-butyl-4-hydroxyphenyl) propionamide] (IRGANOX 1098). Specific processing stabilizers include tris(2,4-di-tert-butylphenyl)phosphite (IRGAFOS 168), 3,9-bis(2,4-di-tert-butylphenoxy)-2,4,8, 10-tetraoxa-3,9-diphosphaspiro[5.5]undecane (IRGAFOS 126), 2,2',2''-nitrilo[triethyl-tris(3,3',5,5'-tetra-tert-butyl-1,1-biphenyl-2,2'-diyl)]phosphite (IRGAFOS 12), and tetrakis (2,4-di-tert-butylphenyl)-[1,1-biphenyl]-4,4'-diylbisphosphonite (IRGAFOS P-EPQ). Specific light stabilizers include 2-(2H-benzotriazole-2-yl)-4,6-bis(1-methyl-1-phenylethyl)phenol (TINUVIN 234), 2-(5-chloro(2H)-benzotriazole-2-yl)-4-(methyl)-6-(tert-butyl)phenol (TINUVIN 326), 2-(2H-benzotriazole-2-yl)-4-(1,1,3,3-tetramethylbutyl)phenol (TINUVIN 329), 2-(2H-benzotriazole-2-yl)-4-(tert-butyl)-6-(sec-butyl)phenol (TINUVIN 350), 2,2'-methylenebis(6-(2H-benzotriazol-2-yl)-4-(1,1,3,3-tetramethylbutyl)phenol) (TINUVIN 360), and 2-(4,6-diphenyl-1,3,5-triazin-2-yl)-5-[(hexyl)oxy]-phenol (TINUVIN 1577), 2-(2'-hydroxy-5'-methylphenyl)benzotriazole (TINUVIN P), 2-hydroxy-4-(octyloxy)benzophenone (CHI-MASSORB 81), 1,3-bis-[(2'-cyano-3',3'-diphenylacryloyl)oxy]-2,2-bis-{[(2'-cyano-3',3'-diphenylacryloyl) oxy]methyl}-propane (UVINUL 3030, BASF), ethyl-2-cyano-3,3-di-phenylacrylate (UVINUL 3035, BASF), and (2-ethylhexyl)-2-cyano-3,3-diphenylacrylate (UVINUL 3039, BASF).

According to a further embodiment the compositions comprise as an optional component the additional flame retardants defined above and additives selected from the group consisting of polymer stabilizers and tetraalkylpiperidine derivatives.

Representative examples of tetraalkylpiperidine derivatives are selected from the group consisting of 1-Cyclohexyloxy-2,2,6,6-tetramethyl-4-octadecylaminopiperidine, bis(1-Octyloxy-2,2,6,6-tetramethylpiperidin-4-yl) sebacate, 2,4-bis[(1-Cyclohexyloxy-2,2,6,6-tetramethylpiperidin-4-yl)butylamino]-6-(2-hy-droxyethylamino-s-triazine, bis(1-Cyclohexyloxy-2,2,6,6-tetramethylpiperidin-4-yl) adipate, 2,4-bis[(1-Cyclohexyloxy-2,2,6,6-tetramethylpiperidin-4-yl)butylamino]-6-chloro-s-triazine, 1-(2-Hydroxy-2-methylpropoxy)-4-hydroxy-2,2,6,6-tetramethylpiperidine, 1-(2-Hydroxy-2-methylpropoxy)-4-oxo-2,2,6,6-tetramethylpiperidine, 1-(2-Hydroxy-2-methylpropoxy)-4-octadecanoyloxy-2,2, 6,6-tetramethyl-piperidine, bis(1-(2-Hydroxy-2-methylpropoxy)-2,2,6,6-tetramethylpiperidin-4-yl) sebacate, bis(1-(2-Hydroxy-2-methylpropoxy)-2,2,6,6-tetramethylpiperidin-4-yl) adipate, 2,4-bis{N-[1-(2-Hydroxy-2-methylpropoxy)-2,2,6,6-tetramethylpiperidin-4-yl]-N-butylamino}-6-(2-hydroxyethylamino)-s-triazine, The reaction product of 2,4-bis[(1-cyclohexyloxy-2,2,6, 6-tetramethylpiperidin-4-yl)butylamino]-6-chloro-s-triazine with N,N'-bis(3-aminopropyl)ethylenediamine), 2,4-bis[(1-Cyclohexyloxy-2,2,6,6-tetramethylpiperidin-4-yl)butylamino]-6-(2-hydroxyethylamino)-s-triazine, The oligomeric compound which is the condensation product of 4,4'-hexame-thylenebis(amino-2,2,6,6-tetramethylpiperidine) and 2,4-dichloro-6-[(1-cyclohexyloxy-2,2,6,6-tetramethylpiperidin-4-yl)butylamino]-s-triazine end-capped with 2-chloro-4,6-bis (dibutylamino)-s-triazine, The compound of the formula

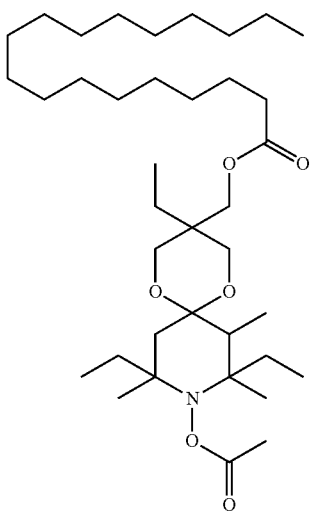 [SMILES: CCCCCCCCCCCCCCCCCC(=O)OCC1(CC)COC2(CC(C)(CC)N(OC(C)=O)C(C)(CC)C2C)OC1]

and the compound of the formula

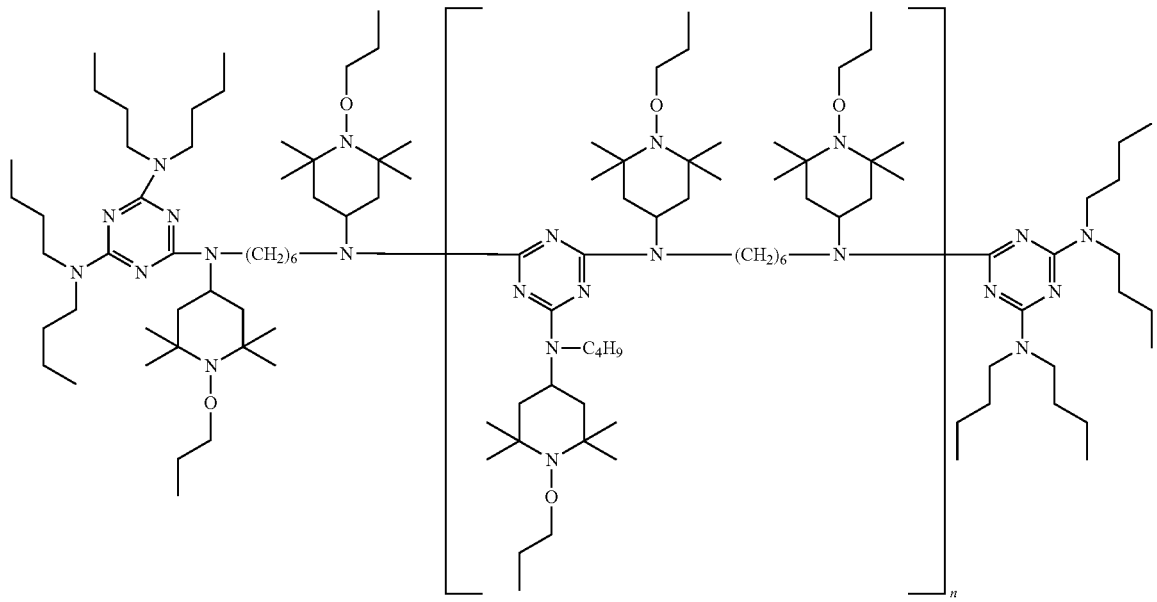

in which n is a numeral from 1 to 15.

The additives mentioned above are preferably contained in an amount of 0.01 to 10.0%, especially 0.05 to 5.0%, relative to the weight of the polymer substrate of Component c).

The incorporation of the components defined above into the polymer component is carried out by known methods such as dry blending in the form of a powder, or wet mixing in the form of solutions, dispersions or suspensions for example in an inert solvent, water or oil. The additive components may be incorporated, for example, before or after molding or also by applying the dissolved or dispersed additive or additive mixture to the polymer material, with or without subsequent evaporation of the solvent or the suspension/dispersion agent. They may be added directly into the processing apparatus (e.g. extruders, internal mixers, etc.), e.g. as a dry mixture or powder, or as a solution or dispersion or suspension or melt.

The addition of the additive components to the polymer substrate can be carried out in customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contra-rotating and co-rotating twin-screw extruders, planetary-gear extruders, ring extruders or co-kneaders. Processing machines provided with at least one gas removal compartment can be used to which a vacuum can be applied.

Suitable extruders and kneaders are described, for example, in *Handbuch der Kunststoffextrusion*, Vol. 1 Grundlagen, Editors F. Hensen, W. Knappe, H. Potente, 1989, pp. 3-7, ISBN:3-446-14339-4 (Vol. 2 *Extrusionsanlagen* 1986, ISBN 3-446-14329-7).

For example, the screw length is 1-60 screw diameters, preferably 35-48 screw diameters. The rotational speed of the screw is preferably 10-600 rotations per minute (rpm), preferably 25-300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components is added, these can be premixed or added individually.

The additive components and optional further additives can also be added to the polymer in the form of a master batch ("concentrate") which contains the components in a concentration of, for example, about 1.0% to about 80.0% and preferably 2.0% to about 60.0% by weight incorporated in a polymer. The polymer is not necessarily of identical structure than the polymer where the additives are added finally. In such operations, the polymer can be used in the form of powder, granules, solutions, and suspensions or in the form of lattices.

The additive components can also be added to the polymer in the form of a master batch ("concentrate") which contains the components in a concentration of, for example, about 1.0% to about 80.0% and preferably 2.0% to about 60.0% by weight incorporated in a polymer. The polymer is not necessarily of identical structure than the polymer where the additives are added finally. In such operations, the polymer can be used in the form of powder, granules, solutions, and suspensions or in the form of lattices. Incorporation can take place prior to or during the shaping operation. The materials containing the additives of the invention described herein preferably are used for the production of molded articles, for example injection molded or roto-molded articles, injection molded articles, profiles and the like, and fibres, spun melt non-woven, films or foams.

A preferred embodiment relates to a process for inducing the flame retardancy in polymers, which comprises adding to a polymer substrate a combination of
a) At least one NOR-HALS compound of the formula

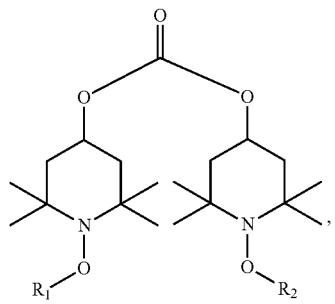

Wherein
$R_1$ and $R_2$ represent $C_1$-$C_{30}$alkyl; with
b) At least one flame retardant compound selected from the group consisting of tris(tribromoneopentyl)phosphate, resorcinol-bis-di phenylphosphate, pentaerythritol-di-methyl phosphonate, guanidine phenylphosphonate, melamine phenylphosphonate, dimethylaluminium phosphinate, methyl-ethyl-aluminiumphosphinate, diethylaluminiumphosphinate, poly-[2,4-(piperazine-1,4-yl)-6-morpholine-4-yl)-1,3,5-triazine] and ammonium polyphosphate.

The polymer substrate suitable for inducing flame retardancy has been described above.

The following Examples illustrate the invention:
A) METHODS

The following standard test methods are used to evaluate the performance of FR-1 as flame retardant:
DIN 4102-Part 1

The specimen is positioned vertically and the ignition flame is applied at the lower edge of the specimen (edge ignition test).

Classification is based on the time for flames to spread 150 mm of the specimen.

If the flame does not reach the 150 mm reference mark within 20 seconds, the tested film passes the test and is classified B2.
UL 94-VTM and UL 94-V A flame is applied twice to the lower end of the test specimen positioned vertically.

UL 94-VTM is a well-known test for classifying the flame retardancy of very thin material in 3 classes VTM-0, VTM-1 and VTM-2. The best rating is VTM-0.

UL 94 test for *Flammability of Plastic Materials for Parts in Devices and Appliances,* 5th edition, Oct. 29, 1996. Ratings according to the UL 94 V test are compiled in the following table (time periods are indicated for one specimen):

TABLE

| Rating | After flame time [sec] | Burning drips | Burn to clamp |
|---|---|---|---|
| V-0 | <10 | No | No |
| V-1 | <30 | No | No |
| V-2 | <30 | Yes | No |
| n.c. | <30 |  | Yes |
| n.c. | >30 |  | No | n.c.: not classified

FR-1

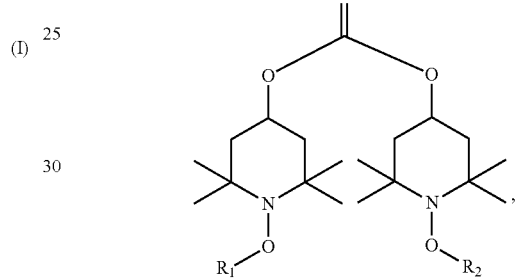

$R_1$, $R_2$: n-undecyl

B) APPLICATION EXAMPLES

Example 1

Flame Retardancy of Fiber Grade Polypropylene (MFI 25) Containing 1% of FR-1
PP Film Manufacture:

Fiber grade polypropylene (Moplen® HP 552 (Basell)) is dry blended with 1% of FR-1 and melt compounded into pellets on a co-rotating twin-screw extruder type Berstorff 32D (lab size twin screw extruder, 25 mm screw diameter, 9 heating zones) at a temperature $T_{max}$ of 230° C.

The pelletized fully formulated resin is cast at a maximum temperature $T_{max}$ of 200° C. into 250 μm films using a cast film equipment Collin CR-136/350 coupled with an extruder Collin E 30 M.

Produced films and concentration of additive are listed in Table 1:

TABLE 1

| Concentration of added additive in the PP film | |
|---|---|
| Film No. | Additive |
| Film 1 | No addition |
| Film 2 | 1% FR-1 |

Performance of FR-1 as Flame Retardant:

TABLE 2

Flame test on 250 μm PP cast films according to modified DIN 4102-Part 1 (edge ignition)

| Film No. | Burning time [sec] | Damaged length [mm] | Burning drips paper ignition [f] | DIN 4102-B2 Rating |
|---|---|---|---|---|
| Film 1 | 33 | 190 | yes | not classified |
| Film 2 | 8 | 62 | no | B2 |

[f] Rated "yes", if the burning drips ignite the paper placed underneath the test specimen according to the DIN 4102-Part 1 test norm.

The burning time of Film 2 containing 1% FR-1 decreases significantly in comparison to Film 1. Film 2 is classified as B2. FR-1 contributes to lower the burning time and the damaged length and, therefore, increases flame retardancy of polypropylene.

TABLE 3

Flame test on 250 μm PP cast films according to UL94-VTM

| Film No. | Average flaming time [a] [sec] | Specimen burnt to holding clamp | UL94-VTM Rating |
|---|---|---|---|
| Film 1 | 31 | Yes | not classified |
| Film 2 | 13 | No | VTM-2 |

[a] Average flaming time per specimen and after maximum 2 ignitions

The efficacy of FR-1 as a flame retardant is demonstrated by a lower average flaming time, with no specimen burnt to the clamp and VTM-2 classification.

Example 2

Flame retardancy of Cast Film Grade Polypropylene (MP 8) Containing 1% of FR-1

PP Film Manufacture:

Fiber grade polypropylene (RD204CF (Borealis)) is dry blended with 1% of FR-1 and melt compounded into pellets on a co-rotating twin-screw extruder type Berstorff 46D (lab size twin screw extruder, 25 mm screw diameter at a temperature $T_{max}$ of 250° C.

The pelletized fully formulated resin is cast at a maximum temperature $T_{max}$ of 230° C. into 250 μm films using a cast film equipment Collin CR-136/350 coupled with an extruder Collin E 30 M.

Produced films and concentration of additive are listed in Table 4.

TABLE 4

Concentration of added additive in the PP film

| Film No. | Additive |
|---|---|
| Film 1 | No addition |
| Film 2 | 1% FR-1 |

Performance of FR-1 as Flame Retardant:

TABLE 5

Flame test on 250 μm PP cast films according to modified DIN 4102-Part 1 (edge ignition)

| Film No. | Burning time [sec] | Damaged length [mm] | Burning drips paper ignition [f] | DIN 4102-B2 Rating |
|---|---|---|---|---|
| Film 1 | 30 | 190 | yes | not classified |
| Film 2 | 10 | 77 | no | B2 |

[f] Rated "yes", if the burning drips ignite the paper placed underneath the test specimen according to the DIN 4102-Part 1 test norm.

The burning time of Film 2 containing 1% FR-1 decreases significantly in comparison with Film 1. Film 2 is classified B2. FR-1 contributes to lower the burning time and the damaged length and, therefore, increases the flame retardancy of polypropylene.

TABLE 6

Flame test on 250 μm PP cast films according to UL94-VTM

| Film No. | Average flaming time [a] [sec] | Specimen burnt to holding damp | UL94-VTM Rating |
|---|---|---|---|
| Film 1 | 27 | Yes | not classified |
| Film 2 | 7 | No | VTM-2 |

[a] Average flaming time per specimen and after maximum of 2 ignitions

The efficacy of FR-1 as a flame retardant is demonstrated by a lower average flaming time, with no specimen burnt to the clamp and VTM-2 classification.

Example 3

Flame Retardancy of TPO (Thermoplastic Polyolefin) Membrane Containing 0.8% of FR-1

TPO 1 mm Film Manufacture:

Roofing membrane grade thermoplastic polyolefin (Hifax® CA 10 A Natural (Lyondell Basell Polymers)) is blended on two roll-mill equipment at 160° C. with 2% titanium dioxide pigment, 0.1% calcium stearate and FR-1 and melt compressed at the temperature of 170° C. into 1 mm plaques by using a hot press. Produced plaques and concentration of additives are listed in Table 7.

TABLE 7

Concentration of added additive in the TPO Plaques

| Film No. | Additive |
|---|---|
| Plaque 1 | No FR-1 |
| Plaque 2 | 0.8% FR-1 |

The Test Method According to DIN 4102-Part 1 is Used to Evaluate the Performance of FR-1 as Flame Retardant:

TABLE 8

Flame test on TPO plaques of 1 mm thickness according to modified DIN 4102-Part 1 (edge ignition)

| Film No. | Burning time [sec] | Damaged length [mm] | Burning drips paper ignition f) | DIN 4102-B2 Rating |
|---|---|---|---|---|
| Plaque 1 | 75 | >150 | yes | not classified |
| Plaque 2 | 23 | 50 | yes | B2 | f) Rated "yes", if the burning drips ignite the paper placed underneath the test specimen according to the DIN 4102-Part 1 test norm.

The burning time as well as the damaged length of Plaque 2 containing 0.8% FR-1 decreases significantly in comparison to Plaque 1. As a result, Plaque 2 is classified B2.

FR-1 contributes to lower the burning time and the damaged length and therefore increases thermoplastic polyolefin flame retardancy.

Example 4

Flame Retardancy of Injection Molded Grade Polypropylene (MR 25) Containing FR-1 Polymer Component: MOPLEN HP 552 R (Lyondell Basell (PP))
Flame Retardant Components:
 ADK STAB LA-81 (ADEKA): bis(1-undecanyloxy-2,2,6,6-tetramethylpiperidin-4-yl)carbonate (FR-1)
 Aflammit®TL 1260 (THOR GROUP LIMITED): Pentaerythritol-di-methylphosphonate (FR-2)

PP, FR-1 and FR-2 are premixed in the amounts indicated and melt compounded into pellets on a co-rotating twin-screw extruder Berstorff 32D (lab size twin screw extruder, 25 mm screw diameter) at a maximum temperature $T_{max}$ of 230° C.

UL94-V test specimen of 1.6 mm thickness are prepared by injection molding (Engel EK 65).

TABLE 9

|  | Ref. 1 | Ref. 2 | Inv. 1 |
|---|---|---|---|
| PP | 100 | 84 | 84 |
| FR-1 |  |  | 1 |
| FR-2 |  | 16 | 15 |
| UL 94 V at 1.6 mm | n.c. | V-2 | V-0 |

Ref. (Referential Compositions) 1, 2; Inv. (Inventive Composition) 1: Addition of FR-1 increases significantly the FR performance of the composition in comparison to Referential Compositions 1, 2. The efficacy of FR-1 as a flame retardant is demonstrated by V-0 classification.

Example 5

Flame Retardancy of High Density Polyethylene (HDPE) Containing FR-1
HDPE Film Manufacture:

High density polyethylene (Hostalen® ACP 7740 F2 (Lyondell Basell)) is dry blended with FR-1 and melt compounded into pellets on a co-rotating twin-screw extruder type Collin 42D (lab size twin screw extruder, 25 mm screw diameter) at a maximum temperature $T_{max}$ of 210° C.

The pelletized fully formulated resin is extruded and blown at a maximum temperature $T_{max}$ of 230° C. into film by using a blown film extrusion equipment Collin Type 180/400 coupled with an extruder Collin E 30 P.

Produced films and concentration of additive are listed in Table 10.

TABLE 10

Concentration of added additive in HDPE blown films

| Film No. | Film | Additive |
|---|---|---|
| 1 | 100 μm | No addition |
| 2 | 200 μm | No addition |
| 3 | 100 μm | 1.5% FR-1 |
| 4 | 200 μm | 1.0% FR-1 |

TABLE 11

Flame test on 200 μm HDPE blown films according to DIN 4102-Part 1 (edge ignition)

| Film No. | Burning time [sec] | Damaged length [mm] | Burning drips paper ignition f) | DIN 4102-B2 rating |
|---|---|---|---|---|
| 2 | 31 | >150 | yes | not classified |
| 4 | 11 | 71 | yes | B2 | f) Rated "yes", if the burning drips ignite the paper placed underneath the test specimen according to the DIN 4102-Part 1 test norm.

The burning time of Film 4 containing 1% FR-1 decreases significantly in comparison to Film 2. Film 4 is classified B2. FR-1 contributes to lower the burning time and the damaged length and therefore increases high density polyethylene flame retardancy.

TABLE 12

Flame test on 100 μm HDPE blown films according to UL94-VTM

| Film No. | Average flaming time[a] [sec] | Specimen burnt to holding clamp | UL94-VTM rating |
|---|---|---|---|
| 1 | 16[b] | Yes | not classified |
| 3 | 7 | No | VTM-2 |

[a] Average flaming time per specimen and after maximum 2 ignitions
[b] Specimen completely burnt after the first ignition.

The efficacy of FR-1 as a flame retardant is demonstrated by lower average flaming time, with no specimen burnt to the clamp and VTM-2 classification.

Example 6

Flame Retardancy of Linear Low Density Polyethylene (LLDPE) Containing FR-1
LLDPE Film Manufacture:

Linear low density polyethylene (1002YB (Exxon Mobile)) is dry blended with 1% FR-1 and melt compounded into pellets on a co-rotating twin-screw extruder type Collin 42D (lab size twin screw extruder, 25 mm screw diameter) at a maximum temperature $T_{max}$ of 210° C. The pelletized fully formulated resin is casted at a maximum temperature $T_{max}$ of 190° C. into 100 and 200 μm film by using a cast film equipment Collin CR-136/350 coupled with an extruder Collin E 30 M.

Produced films and concentration of additive are listed in Table 13.

TABLE 13

Concentration of added additive in the LLDPE cast film

| Film No. | Film | Additive |
|---|---|---|
| 1 | 100 μm | without addition |
| 2 | 200 μm | without addition |
| 3 | 100 μm | 1.0% FR-1 |
| 4 | 200 μm | 1.0% FR-1 |

TABLE 14

Flame test on 100 and 200 μm LLDPE cast films according to modified DIN 4102-Part 1 (edge ignition)

| Film No. | Burning time [sec] | Damaged length [mm] | Burning drips paper ignition[f] | DIN 4102-B2 Rating |
|---|---|---|---|---|
| Film 1 (100 μm) | 21 | >150 | yes | not classified |
| Film 2 (100 μm) | 3 | 62 | no | B2 |
| Film 3 (200 μm) | 32 | >150 | yes | not classified |
| Film 4 (200 μm) | 6 | 54 | yes | B2 |

[f] Rated "yes", if the burning drips ignite the paper placed underneath the test specimen according to the DIN 4102-Part 1 test norm.

The burning time of Film 2 and 4 containing 1.0% FR-1 decreases significantly in comparison to Film 1 and 3. Film 2 and 4 are classified B2. FR-1 contributes to lower the burning time and the damaged length and, therefore, increases the flame retardancy in low density polyethylene.

TABLE 15

Flame test on 100 and 200 μm LLDPE cast films according to UL94-VTM

| Film No. | Average flaming time[a] [sec] | Specimen burnt to holding clamp | UL94-VTM Rating |
|---|---|---|---|
| Film 1 (100 μm) | 14[b] | Yes | not classified |
| Film 2 (100 μm) | 4 | No | VTM-2 |
| Film 3 (200 μm) | 23[b] | Yes | not classified |
| Film 4 (200 μm) | 15 | No | VTM-2 |

[a] Average flaming time per specimen and after maximum 2 ignitions
[b] Specimen completely burnt after the first ignition.

The efficacy of FR-1 as a flame retardant is demonstrated by lower average flaming time, with no specimen burnt to the clamp and VTM-2 classification.

The invention claimed is:

1. A composition, which comprises
a) an NOR-HALS compound of the formula

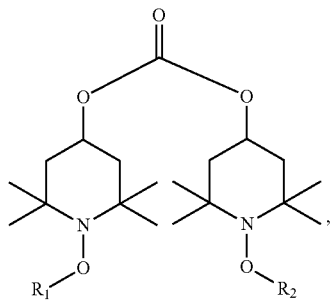

(I)

wherein
R$_1$ and R$_2$ represent n-undecyl;
b) at least one flame retardant compound selected from the group consisting of guanidine phenylphosphonate and melamine phenylphosphonate; and
c) a polymer substrate.

2. The composition according to claim 1, wherein said composition further comprises at least one additional flame retardant compound selected from the group consisting of dimethylaluminium phosphinate, methyl-ethyl-aluminium-phosphinate, diethylaluminiumphosphinate, and poly-[2,4-(piperazine-1,4-yl)-6-morpholine-4-yl)-1,3,5 triazine].

3. The composition according to claim 1, which further comprises at least one additional flame retardant or additive selected from the group consisting of a tetraalkylpiperidine additive, a polymer stabilizer, a filler, a reinforcing agent, a glass fibre, a polytetrafluoroethylene (PTFE), a carbon fibre, and a glass sphere.

4. The composition according to claim 3, which comprises as an additional flame retardant a nitrogen containing compound selected from the group consisting of melamine polyphosphate, ammonium polyphosphate, melamine ammonium phosphate, melamine ammonium polyphosphate, melamine ammonium pyrophosphate, a condensation product of melamine with phosphoric acid and other reaction products of melamine with phosphoric acid and mixtures thereof.

5. A process for inducing the flame retardancy in polymers, which comprises adding to a polymer substrate a combination of
a) an NOR-HALS compound of the formula

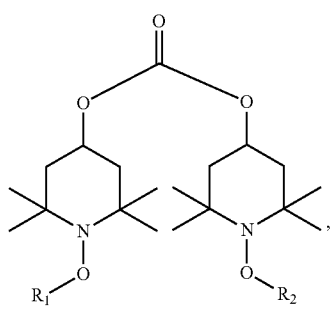

(I)

wherein
R$_1$ and R$_2$ represent n-undecyl; with
b) at least one flame retardant compound selected from the group consisting of guanidine phenylphosphonate and melamine phenylphosphonate.

6. The process according to claim 5, which further comprises adding to said polymer substrate at least one additional flame retardant compound selected from the group consisting of dimethylaluminium phosphinate, methyl-ethyl-aluminiumphosphinate, diethylaluminiumphosphinate, and poly-[2,4-(piperazine-1,4-yl)-6-morpholine-4-yl)-1,3,5 triazine].

7. The process according to claim 5, which further comprises adding to said polymer substrate at least one additional flame retardant or additive selected from the group consisting of a tetraalkylpiperidine additive, a polymer stabilizer, a filler, a reinforcing agent, a glass fibre, a polytetrafluoroethylene (PTFE), a carbon fibre, and a glass sphere.

8. The process according to claim 7, which comprises as an additional flame retardant a nitrogen containing compound selected from the group consisting of melamine polyphosphate, ammonium polyphosphate, melamine ammonium phosphate, melamine ammonium polyphosphate, melamine ammonium pyrophosphate, a condensation product of melamine with phosphoric acid and other reaction products of melamine with phosphoric acid and mixtures thereof.

* * * * *

UNITED STATES PATENT AND TRADEMARK OFFICE
CERTIFICATE OF CORRECTION

PATENT NO. : 10,316,169 B2
APPLICATION NO. : 15/700748
DATED : June 11, 2019
INVENTOR(S) : Gerard Lips et al.

It is certified that error appears in the above-identified patent and that said Letters Patent is hereby corrected as shown below:

In the Specification

In Column 4, Line 14, delete "iso-prene" and insert -- isoprene --;
     Line 16, delete "propy-lene" and insert -- propylene --.

In Column 8, Lines 9-10, delete "terephtha-late-resorcinol" and insert -- terephthalate-resorcinol --, therefor.

Signed and Sealed this
Twenty-first Day of April, 2020

Andrei Iancu
*Director of the United States Patent and Trademark Office*